United States Patent [19]

Aday

[11] Patent Number: 4,491,218
[45] Date of Patent: Jan. 1, 1985

[54] SINGLE SUTURE STRAND DISPENSER PACKAGE

[75] Inventor: Jorge L. Aday, Lambertville, N.J.

[73] Assignee: Ethicon, Inc., Somerville, N.J.

[21] Appl. No.: 532,633

[22] Filed: Sep. 15, 1983

[51] Int. Cl.³ .............................................. A61L 17/02
[52] U.S. Cl. ..................... 206/63.3; 206/388; 206/491
[58] Field of Search .................. 206/63.3, 388, 491, 206/353, 392; 242/174

[56] References Cited

U.S. PATENT DOCUMENTS

| 3,136,418 | 6/1964 | Stacy et al. | 206/63.3 |
| 3,357,550 | 12/1967 | Holmes et al. | 206/63.3 |
| 3,728,839 | 4/1973 | Glick | 206/63.3 |
| 3,869,044 | 3/1975 | Olsson et al. | 206/63.3 |
| 4,258,843 | 3/1981 | Wymer | 206/63.3 |
| 4,287,987 | 9/1981 | Hoffman et al. | 206/63.3 |
| 4,412,614 | 11/1983 | Ivanov et al. | 206/63.3 |

Primary Examiner—Joseph Man-Fu Moy
Attorney, Agent, or Firm—Robert L. Minier

[57] ABSTRACT

An elongated, multi-paneled, foldable retainer for sterile sutures. Sutures are wound about a winding panel so as to be disposed inwardly from the edges of the retainer and the sutures are held in that position by a suture retaining panel.

4 Claims, 6 Drawing Figures

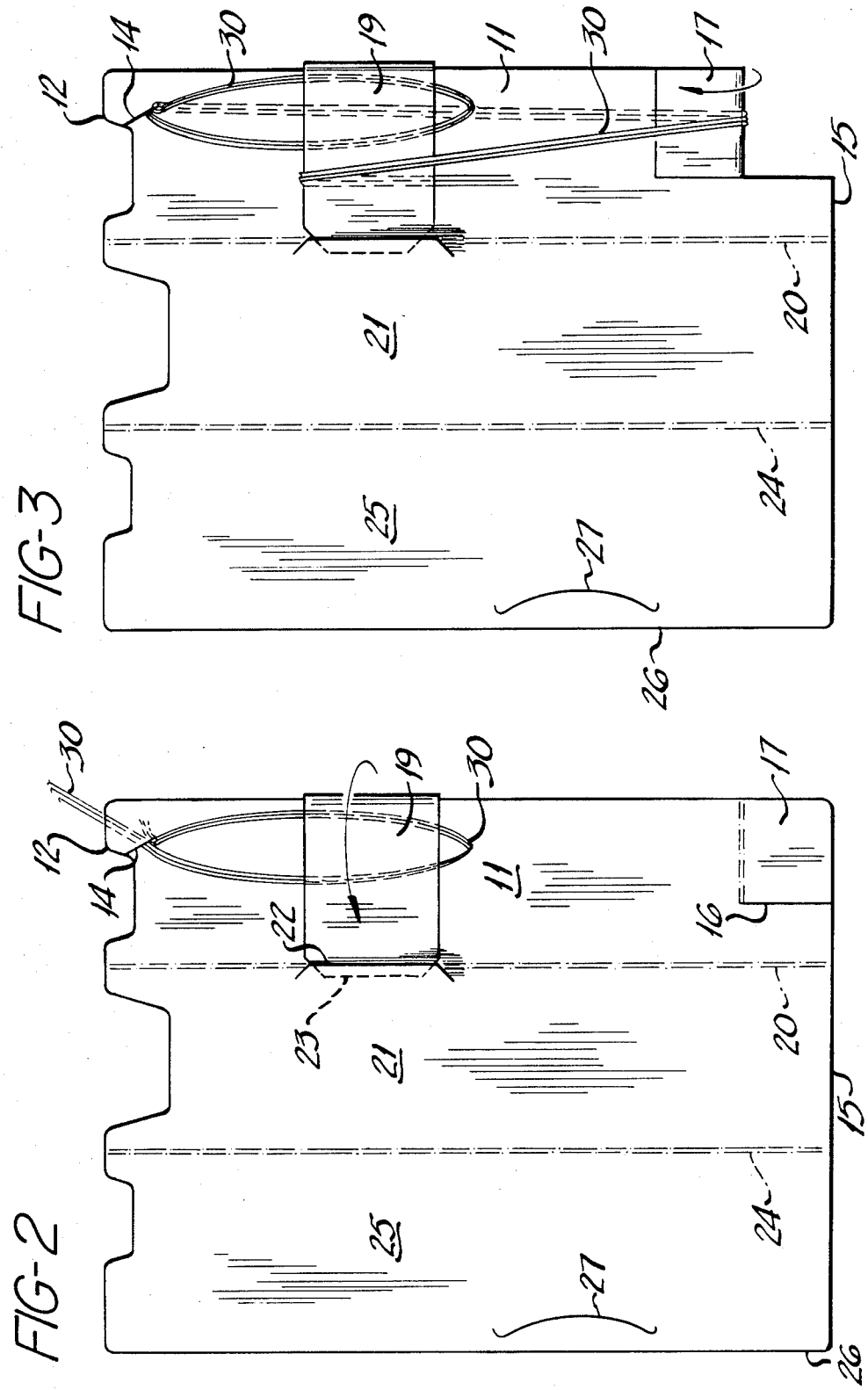

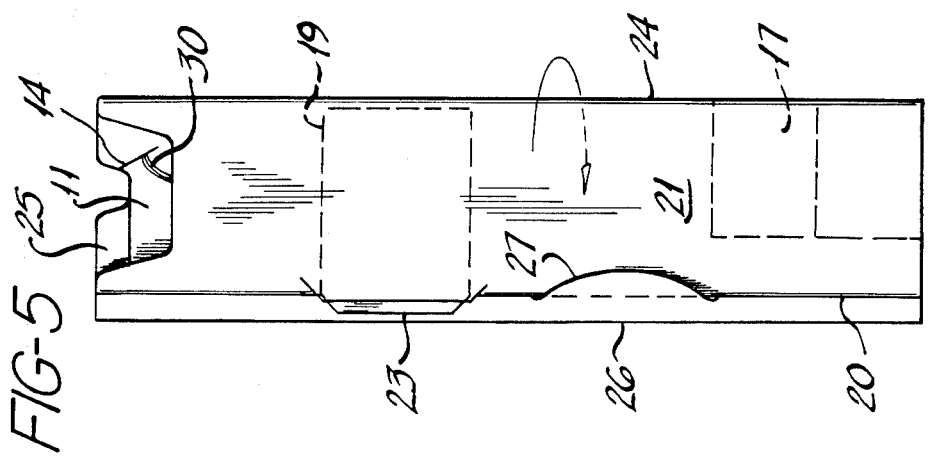
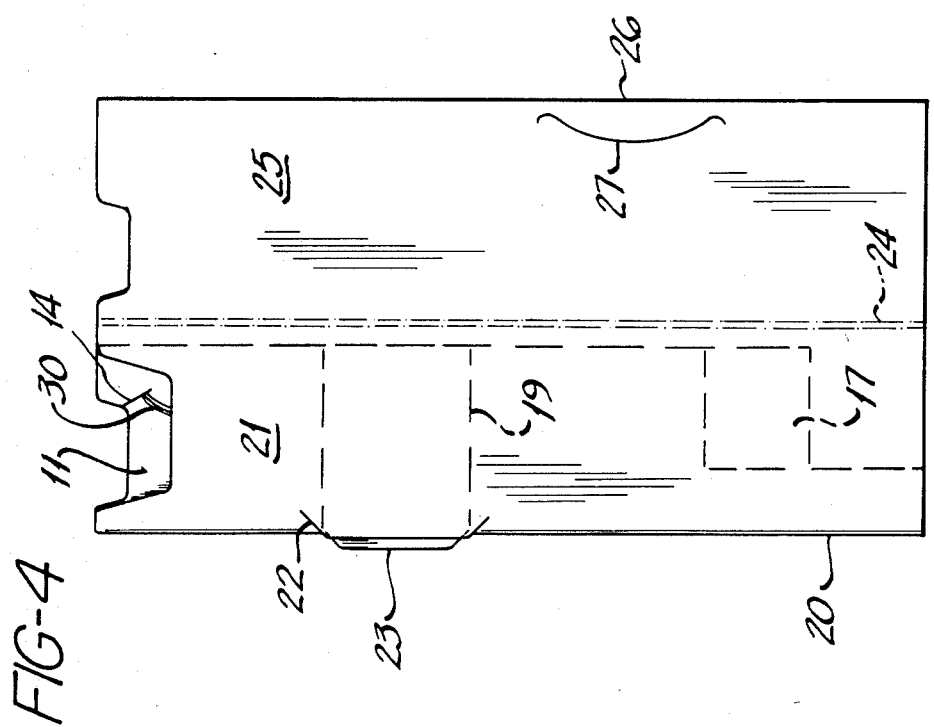

4,491,218

SINGLE SUTURE STRAND DISPENSER PACKAGE

BACKGROUND OF THE INVENTION

The present invention relates to packages for surgical sutures and more particularly to a multiple panel folder retainer for a plurality of sutures which allows for single strand dispensing of the sutures.

Packages for surgical sutures are constructed according to the nature of the suture and its intended use. Also, the packages are designed taking into consideration the economics of the package and the method of placing the sutures in the package. In general, the ideal package protects the suture during handling and storage yet allows the suture to be removed with a minimum of difficulty and the package itself is economical to produce.

The more popular suture packages consist of a folded paper retainer with the suture therein and with the retainer contained in a sterile hermetically sealed envelope. In many instances, the sterility of the suture and envelope are maintained by a second sealed outerwrap. When the suture is to be used, the outerwrap is opened in the operating room and the sealed envelope deposited in a sterile area. Sterile personnel thereupon tear open the sterile envelope to gain access to the suture.

Many packages have been developed to provide either easy access or simplified winding of the suture or ready dispensing of single sutures from the package and the like. Representative packages are more fully described in U.S. Pat. Nos. 3,936,696; 3,280,971; 3,490,192; 4,089,409; 4,126,221; 4,253,563; and 4,249,656.

The present invention presents a very simplified suture package. The package is very inexpensive to produce and the methods for placing the sutures in the package and folding the package are very simple and extremely economical.

The retainers of the present invention may hold sutures of varying lengths from 20 to 100 cm. or even shorter or longer sutures and sutures of various sizes as desired. The retainers and packages of the present invention may contain a single suture but in their preferred form they contain a plurality of sutures and readily present strands of single sutures for dispensing. These and other objects of the present invention will be apparent from the ensuing description and claims.

SUMMARY OF THE INVENTION

The present invention provides an elongated multi-panel folded suture retainer for sutures. The retainer has a suture winding panel. The panel is an elongated panel and includes a slit in one shorter edge thereof. This slit is used for retaining suture ends of loops placed in the slit. In preferred embodiments of the retainer of the present invention, a portion of this shorter edge is disposed inwardly from the remainder of the shorter edge and that inwardly disposed portion contains the slit. A portion of the opposite shorter edge of the suture winding panel is foldable inwardly to reduce the length of the suture winding panel across at least a portion of the width of said panel whereby sutures retained in the slit may be longitudinally wound about the suture winding panel and the final wound suture is disposed inwardly from the outer edges of the finally folded retainer. A suture retainer panel is foldably connected to a portion of the longitudinal edge of the winding panel. First and second suture covering panels are attached to the winding panel with the first suture covering panel being foldably connected to the suture winding panel along the opposite longitudinal edge of said winding panel. The second suture covering panel is foldably connected to the longitudinal edge of the first suture covering panel. A slit is disposed in the longitudinal edge connecting the suture winding panel and the first suture covering panel. The suture retaining panel may be folded on the sutures wound on the suture winding panel and the free edge of said suture retaining panel interlocked with the slit thereby holding the wound sutures in place. A curved slit is disposed adjacent the longitudinal edge of the second suture winding panel to lock the retainer in its fully folded condition. In certain preferred embodiments of the present invention, the folded retainer with a plurality of sutures disposed therein is hermetically sealed in an outer envelope. Preferably the outer envelope comprises a pair of heat sealable films sealed about the periphery of the folded retainer to hermetically seal the folded retainer containing the sutures therein.

The invention will be more fully described when taken in conjunction with the accompanying drawings.

DESCRIPTION OF THE DRAWING

FIG. 2 is a plan view of the retainer of FIG. 1 illustrating the initial placement of the sutures with that placement being retained and placed by folding the suture retaining panel by the suture retaining panel;

FIG. 3 is a plan view of the retainer of FIG. 1 with the foldable portion of the suture winding panel folded in place and the sutures appropriately wound about said suture winding panel;

FIG. 4 is a plan view of the suture retainer of FIG. 1 with sutures in place and with the suture covering panel initially folded on the suture winding panel;

FIG. 5 is a plan view of the fully folded suture retainer of FIG. 1; and

DETAILED DESCRIPTION OF THE INVENTION

Figure 1:
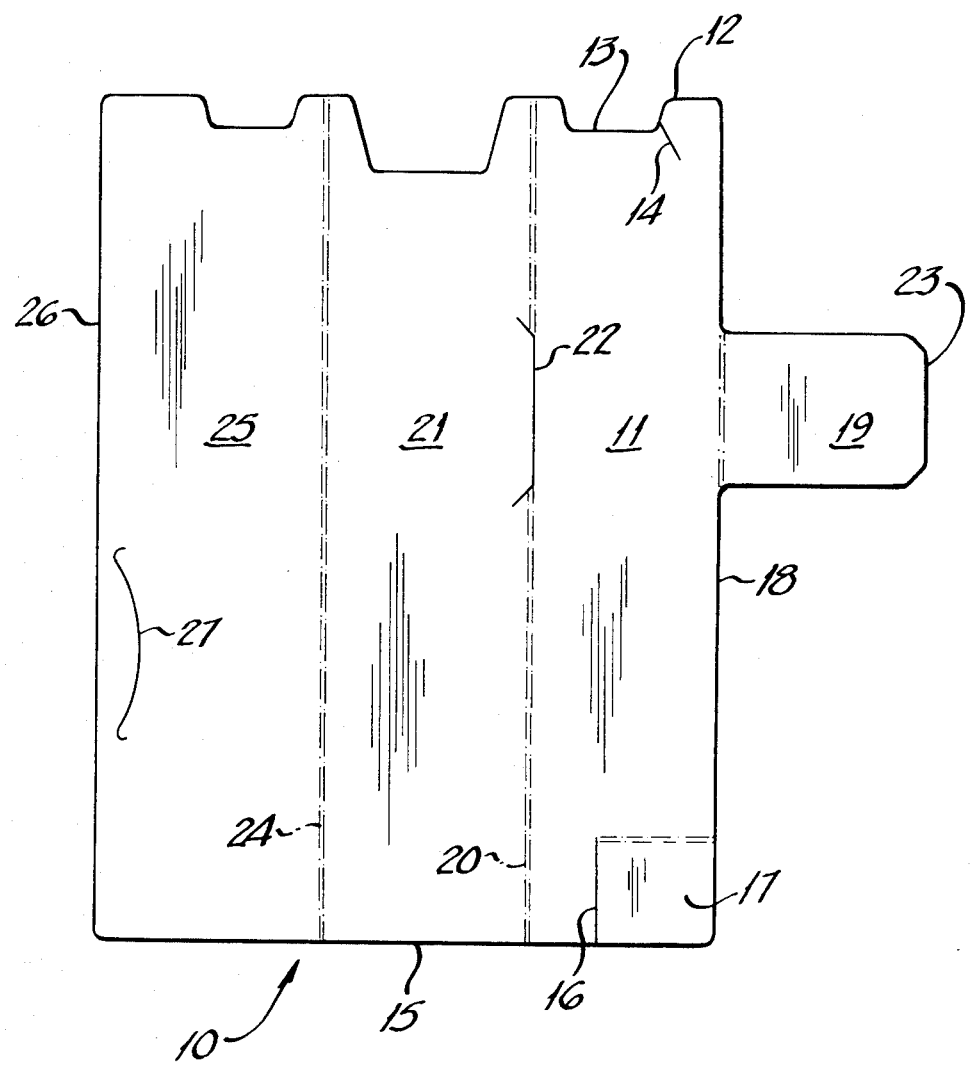
FIG. 1 is a plan view of an unfolded suture retainer of the present invention.

FIGS. 1 through 5 illustrate the various stages in preparing and folding the retainer of the present invention. In FIG. 1 there is illustrated an unfolded suture retainer 10. The retainer comprises a suture winding panel 11. The shorter edge 12 of this panel has a section 13 disposed inwardly and in that section there is disposed a slit 14. The opposite shorter edge 15 of this winding panel contains a slit 16 to allow for a portion 17 of that edge to be folded inwardly. Connected to a portion of one of the longitudinal edges 18 of the suture winding panel is a suture retaining panel 19. The width of the retaining panel is substantially the same as the width of the suture winding panel. Attached to the opposite longitudinal edge 20 of the suture winding panel is a first suture covering panel 21. Disposed in the longitudinal edge 20 between the suture winding panel and the suture covering panel is a slit 22. The slit is disposed so as to engage the free end 23 of the suture retaining panel when the suture retaining panel is folded about the suture winding panel. Foldably connected to the opposite longitudinal edge 24 of the first suture covering panel 21 is a second suture covering panel 25.

Disposed adjacent the free longitudinal edge 26 of the second suture covering panel is a curved slit 27 for locking the entire folder retainer together.

As more clearly depicted in FIG. 2, sutures 30 of appropriate length are first folded in half and the sutures adjacent the looped portion 31 are inserted in the slit 14 in the shorter edge 12 of the suture winding panel 11. The loop is retained by the suture holding panel 19 which is folded over the suture winding panel with the free end 23 engaged in the slit 22.

As more clearly shown in FIG. 3, the foldable section 17 at the bottom edge 15 of the suture winding panel 11 is folded inwardly and the sutures 30 wound about the suture winding panel and engaged by the suture retaining panel 19.

As more clearly shown in FIGS. 4 and 5, the suture covering panels 21 and 25 are folded on top of the suture winding panel 11 with the suture 30 wound around that panel. The second suture winding panel 25 is folded further behind the suture winding panel and the curved slit 27 engaged with the folded edge 20 joining the suture winding panel to the first suture covering panel to lock the retainer in place.

Figure 6:
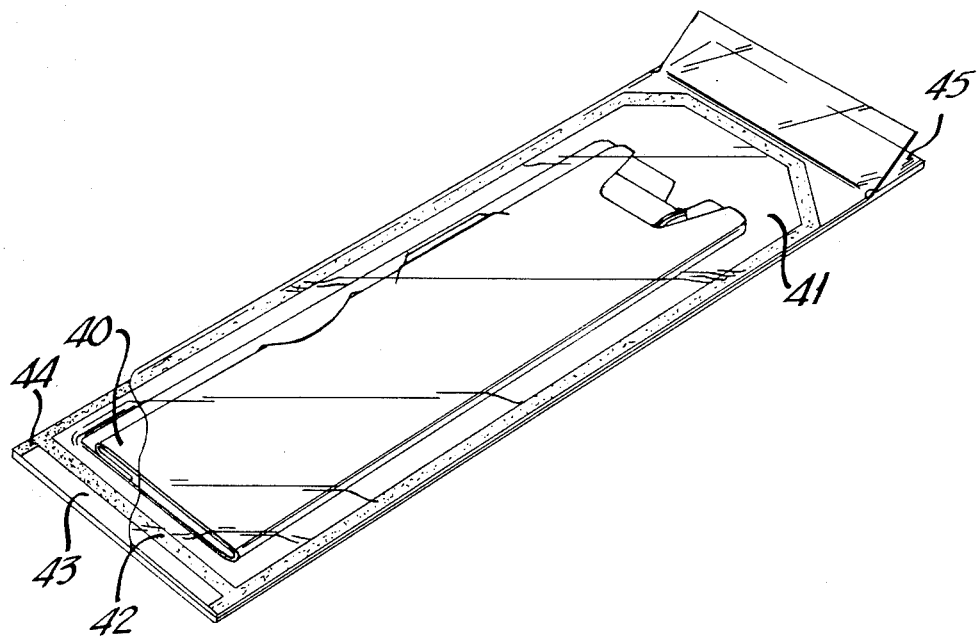
FIG. 6 is a perspective view with portions cut away of a fully folded suture retainer of FIG. 1 contained within a sealed outer envelope.

As depicted in FIG. 6 the fully folded suture retainer 40 is subsequently sealed and sterilized within a sterile outer envelope 41 as illustrated in the FIG. 6. The envelope is a conventional suture package envelope formed by heat sealing the panels 42 and 43, (one of a nonwoven fabric and the other of a thermoplastic film coated on their interior surfaces with a heat sealable polymeric composition 44) together. The envelope is bonded together around the periphery of the inner folded retainer as illustrated. Other means for sealing the envelope may be used at the discretion of the practioner. The very outer edge 45 at one of the shorter edges of the envelope is left unsealed to allow for the easy peeling away of the two outer layers to readily expose the folded suture retainer.

Sutures packaged as illustrated in FIG. 6 are sterile and hermetically sealed and may be stored for extended periods of time. When the suture is to be removed from the package, the outer envelope is opened to expose a sterile suture and suture retainer.

The suture retainers of the present invention are preferably constructed of a heavy weight, relatively stiff sulfate paperboard. This paperboard is relatively foldable and yet sufficiently strong and stiff to support the suture and provide a rigid package. Other materials, including plastics, foils, and laminates combined with each other or with paper, may also be used. The retainers of the present invention may contain a single suture or a plurality of sutures and the retainers may contain sutures of varying sizes and lengths as desired.

The preceding description has been directed primarily to a preferred embodiment of the present invention and many variations which nevertheless employ the features thereof will be apparent to those skilled in the art. Such variations are included within the scope of the present invention.

What is claimed is:

1. An elongated multi-paneled, foldable retainer for sterile sutures comprising:
   (a) a suture winding panel, said panel including a slit in one shorter edge thereof for retaining sutures placed therein,
   (b) a portion of the other shorter edge of said suture winding panel being foldable inwardly to reduce the length of said suture winding panel over a portion of the width of said panel whereby sutures retained in said slit may be longitudinally wound about said suture winding panel and the final wound suture disposed inwardly from the outer edges of said finally folded retainer,
   (c) a suture retaining panel foldably connected to a portion of a longitudinal edge of said winding panel,
   (d) first and second suture covering panels, said first suture covering panel being foldably connected to said suture winding panel, and said second suture covering panel being foldably connected to a longitudinal edge of said first suture covering panel,
   (e) said first suture covering panel being shortened over at least a portion of the width of the panel at the shorter edge of said panel that is meant to overlie the shorter edge of the suture winding panel containing said slit whereby a portion of the suture is exposed in the final folded retainer,
   (f) a slit in the edge connecting said suture winding panel and said first suture covering panel for interlocking the free end of said suture retaining panel to said edge, thereby holding the wound sutures in place,
   (g) a curved slit adjacent the free longitudinal edge of said second suture covering panel to engage the folded edge of the first suture covering panel and the suture winding panel to lock the retainer in its folded position.

2. An enlongated retainer according to claim 1 wherein a portion of the shorter edge of the suture winding panel containing the slit for retaining sutures is disposed inwardly from the remainder of said shorter edge of said winding panel.

3. An elongated retainer for sutures according to claim 1 or 2 containing a plurality of sutures wound about the suture winding panel.

4. A suture package comprising the retainer of claim 1 or 2 enclosed in an outer envelope sealed about the periphery of said folded retainer.

* * * * *